(12) United States Patent
Rueter et al.

(10) Patent No.: US 7,130,690 B2
(45) Date of Patent: Oct. 31, 2006

(54) ATRIAL CAPTURE MANAGEMENT DURING ATRIAL AND VENTRICULAR PACING

(75) Inventors: John C. Rueter, Woodbury, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 503 days.

(21) Appl. No.: 10/625,344

(22) Filed: Jul. 23, 2003

(65) Prior Publication Data

US 2005/0021095 A1     Jan. 27, 2005

(51) Int. Cl.
*A61N 1/362* (2006.01)

(52) U.S. Cl. .................. 607/28; 607/9; 607/25; 607/27

(58) Field of Classification Search .............. 607/9, 607/25, 27, 28
See application file for complete search history.

(56) References Cited

U.S. PATENT DOCUMENTS

| | | | |
|---|---|---|---|
| 3,920,024 A | 11/1975 | Bowers ................ | 128/419 PG |
| 4,428,378 A | 1/1984 | Anderson et al. ...... | 128/419 PG |
| 4,686,988 A | 8/1987 | Sholder ................ | 128/419 PT |
| 4,890,617 A | 1/1990 | Markowitz et al. ... | 128/419 PG |
| 5,144,949 A | 9/1992 | Olson .................... | 128/419 PG |
| 5,165,404 A | 11/1992 | Anderssson et al. .. | 128/419 PG |
| 5,165,405 A | 11/1992 | Eckwall ................ | 128/419 PG |
| 5,172,690 A | 12/1992 | Nappholz et al. ..... | 128/419 PG |
| 5,222,493 A | 6/1993 | Sholder ................ | 128/419 P |
| 5,285,780 A | 2/1994 | Tsuji et al. ............ | 607/13 |
| 5,320,643 A | 6/1994 | Roline et al. ......... | 607/28 |
| 5,324,310 A | 6/1994 | Greeninger et al. ... | 607/28 |
| 5,331,966 A | 7/1994 | Bennett et al. ....... | 128/696 |
| 5,476,486 A | 12/1995 | Lu et al. ............... | 607/28 |
| 5,476,487 A | 12/1995 | Sholder ................ | 607/28 |
| 5,564,430 A | 10/1996 | Jacobson et al. ..... | 128/697 |
| 5,601,615 A | 2/1997 | Markowitz et al. ... | 607/28 |
| 5,626,623 A | 5/1997 | Kieval et al. ......... | 607/23 |
| 5,674,254 A | 10/1997 | van Krieken ......... | 607/11 |
| 5,683,426 A | 11/1997 | Greenhut et al. ..... | 607/9 |
| 5,683,431 A | 11/1997 | Wang .................... | 607/28 |
| 5,861,012 A | 1/1999 | Stroebel ................ | 607/28 |
| 5,861,013 A | 1/1999 | Peck et al. ............ | 607/28 |
| 5,902,324 A | 5/1999 | Thompson et al. ... | 607/9 |
| 6,134,473 A | 10/2000 | Hemming et al. .... | 607/28 |
| 6,144,881 A | 11/2000 | Hemming et al. .... | 607/28 |
| 6,216,037 B1 | 4/2001 | Van Oort .............. | 607/28 |

(Continued)

FOREIGN PATENT DOCUMENTS

EP          0 850 662 A2     7/1998

(Continued)

*Primary Examiner*—Robert Pezzuto
*Assistant Examiner*—Shevon Johnson
(74) *Attorney, Agent, or Firm*—Girma Wolde-Michael; Daniel G. Chapik

(57) ABSTRACT

In an atrial pacing system, the A-PACE pulse energy, defined by the pulse width and pulse amplitude, sufficient to reliably capture the atrium without being wasteful of battery energy is periodically determined in accordance with atrial capture management (ACM) algorithms. The ACM algorithms allow a slow intrinsic atrial heart rate that is suppressed by delivered A-PACE pulses resulting in A-CAPTURE and that occurs when delivered test A-PACE pulses result in ALOC to be detected. ALOC is declared if an A-EVENT of the slow intrinsic atrial heart rate is detected either during an ACM test window timed from the last delivered test A-PACE pulse or during delivery of a sequence of test A-PACE pulses delivered within or defining the ACM test window correlated to the slow intrinsic atrial heart rate.

22 Claims, 7 Drawing Sheets

U.S. PATENT DOCUMENTS

| | | |
|---|---|---|
| 6,311,088 B1 | 10/2001 | Betzold et al. ............... 607/14 |
| 6,389,316 B1 * | 5/2002 | Bornzin et al. ............... 607/28 |
| 6,584,354 B1 | 6/2003 | Mann et al. |
| 6,587,723 B1 | 7/2003 | Sloman et al. |

FOREIGN PATENT DOCUMENTS

EP    1 155 712 A2    11/2001

* cited by examiner

ATRIAL CAPTURE MANAGEMENT DURING ATRIAL AND VENTRICULAR PACING

RELATED APPLICATIONS

This disclosure is related to the following co-pending U.S. patent application Ser. No. 10/260,984 filed Sep. 30, 2002, entitled METHOD AND APPARATUS FOR PERFORMING STIMULATION THRESHOLD SEARCHES by C. M. Manrodt et al., and co-pending U.S. patent application Ser. Nos. 10/004,164 filed Oct. 30, 2001, and Ser. No. 10/434,689 filed May 9, 2003, both for CAPTURE MANAGEMENT IMPROVEMENTS by John C. Rueter et al., which are not admitted as prior art with respect to the present disclosure by mention in this section.

Field of the Invention

This invention relates to implantable AV synchronous, dual chamber pacing systems, and particularly to improved determination of atrial capture during atrial pacing.

BACKGROUND OF THE INVENTION

Atrial synchronized, dual chamber, pacing modes, particularly, the multi-programmable, VDD, VDDR, DDD and DDDR pacing modes, have been widely adopted in implantable dual chamber pacemakers for providing atrial and ventricular or AV synchronized pacing on demand. Such dual chamber pacing modes have also been incorporated into implantable cardioverter/defibrillators (ICDs) and into right and left heart pacing systems providing synchronized right and left heart pacing for enhancing left ventricular cardiac output as described in commonly assigned U.S. Pat. No. 5,902,324.

Such pacing systems are embodied in an implantable pulse generator (IPG) adapted to be subcutaneously implanted and at least atrial and ventricular pacing or cardioversion/defibrillation leads that are coupled to the IPG. The atrial and ventricular leads each incorporate one or more lead conductor that extends through the lead body to an exposed pace/sense electrode or cardioversion/defibrillation electrode disposed in operative relation to a heart chamber.

The pacing operating system comprises atrial and ventricular sense amplifiers and atrial and ventricular pace pulse generators. The atrial sense amplifier is coupled to active and indifferent atrial pace/sense electrodes to detect electrical signals of the heart associated with atrial depolarizations (P-waves) and to generate an atrial sense event (A-EVENT) signal when detection criteria are met. The ventricular sense amplifier is coupled to active and indifferent ventricular pace/sense electrodes to detect electrical signals of the heart associated with ventricular depolarizations (R-waves) and to generate a ventricular sense event (V-EVENT) signal when detection criteria are met. The atrial pace pulse generator delivers a negative-going or cathodal voltage atrial pacing (A-PACE) pulse through a pacing path comprising the active and indifferent atrial pace/sense electrode. The ventricular pace pulse generator delivers a negative-going or cathodal voltage atrial pacing (V-PACE) pulse through a pacing path comprising the active and indifferent ventricular pace/sense electrode.

The pacing operating system times out various intervals from each A-EVENT, V-EVENT, A-PACE, and V-PACE to maintain synchronous depolarizations of the atria and ventricles. Such AV synchronous pacemakers that perform this function have the capability of tracking the patient's natural sinus rhythm and preserving the hemodynamic contribution of the atrial contraction over a wide range of heart rates. Maintenance of AV mechanical synchrony is of great importance as set forth in greater detail in commonly assigned U.S. Pat. No. 5,626,623.

Each of the A-PACE and V-PACE pulse energies is set at a programmable energy level, involving both pulse width (duration) and amplitude (strength), so as to provide sufficient energy to cause the heart chamber to depolarize and contract. The minimum pacing pulse energy which is required to capture and thus evoke a muscular depolarization within the heart is referred to as the "stimulation threshold", and generally varies in accordance with the well known strength-duration curves, wherein the amplitude of a stimulation threshold current pulse and its duration are inversely proportional. When a delivered pacing pulse is successful in so stimulating the heart into contraction, it is said to have "captured" the heart, whereas failure to stimulate the heart is described as "loss of capture" (LOC).

In order to maximize the useful life of dual chamber pacing IPGs, it is desirable that the A-PACE pulse energy and the V-PACE pulse energy be programmed to the minimal energies required to capture the atria and ventricles, respectively. As is well known, the stimulation threshold for a patient, in both the atrium and the ventricle, can fluctuate both short term and long term following implantation. The A-PACE and V-PACE pulse energies are therefore typically programmed by the physician at implantation employing an external programmer to exceed the stimulation threshold by a "safety margin" to avoid atrial loss of capture (ALOC) and ventricular loss of capture (VLOC).

As described in commonly assigned U.S. Pat. No. 5,324,310, the post-operative determination of the stimulation thresholds by the physician typically requires the patient to be connected to surface ECG equipment while a threshold routine is conducted using the pacemaker programmer. The pacemaker programmer successively reprograms the pulse width and/or amplitude on a temporary basis to ascertain the points at which capture is lost. The A-PACE and/or V-PACE pulses are observed on a display or paper tracing as spikes, and capture or LOC is observed by the presence or absence of the "evoked response" wave shape (a P-wave or an R-wave) that follows each spike. At LOC, the programmed pacing pulse may be immediately restored so that the patient does not experience syncope. A strength-duration curve may be plotted from the resulting threshold data. The resulting threshold data may then be used to permanently reprogram the pulse energy. Naturally, such periodic patient studies are time-consuming and expensive to conduct. Moreover, they do not provide an indication of stimulation threshold fluctuation over the course of a patient's day and levels of activity.

Therefore, systems and methods have been proposed to be incorporated or have been incorporated into the IPG operating system to periodically, automatically conduct stimulation threshold tests, and to readjust the pacing pulse energy in relation to any newly determined stimulation threshold. See, for example, U.S. Pat. No. 3,920,024, where the pacing pulse energy is initially set at a high enough energy to ensure capture, and then is reduced by successive increments until LOC is detected and a back-up pacing pulse is delivered.

The evoked response characteristic of capture is intended to be sensed across a particular pace/sense electrode pair, and LOC is inferred if the evoked response is not detected within a short time window following delivery of the pacing pulse.

However, sensing of the evoked response is rendered difficult for a variety of reasons. The A-PACE and V-PACE pulses are produced by the exponential discharge of respective atrial and ventricular output capacitors through the impedance loads in the atrial and ventricular pacing paths that each include a coupling capacitor, the active and indifferent pace/sense electrodes, and the patient's heart tissue between the pace/sense electrodes. It is conventional to suppress or blank both of the atrial and ventricular sense amplifiers during A-PACE and V-PACE pulses for blanking periods to avoid overloading the sense amplifier, to allow a fast recharge function to be completed, and to prevent sensing of artifacts resulting in false declarations of A-EVENTs or V-EVENTs.

In addition, a number of sense amplifier refractory periods are timed out on atrial and ventricular sense event signals and generation of A-PACE and V-PACE pulses, whereby "refractory" A-EVENT and V-EVENTs during such refractory periods are selectively ignored or employed in a variety of ways to reset or extend time periods being timed out. The durations of the blanking and refractory periods therefore render it difficult to reliably detect an evoked response, if any, across the same pace/sense electrode pair that the A-PACE or V-PACE pulse is delivered across.

As a result of these considerations, a great deal of effort has been expended over many years to develop IPGs having the capability of automatically testing the stimulation threshold, i.e. providing an "auto-capture" detection function, and resetting the pacing pulse energy to exceed the threshold by the safety margin without the need for clinical or patient intervention.

Commonly assigned U.S. Pat. Nos. 6,134,473 and 6,144,881 describe the Capture Management algorithm implemented, for example, in the Medtronic® Kappa® 700 pacemaker IPGs. The polarity of the positive or negative change in voltage with respect to time (or dv/dt) of the waveform incident on the pace/sense electrodes is monitored during a short period of time immediately following a paced event. In one embodiment, sensing of the evoked response is based upon a relationship between a maximum magnitude of a derivative of a sensed signal and a predetermined threshold reference value. The evoked response is declared when the maximum amplitude of the derivative of the sensed signal equals or exceeds the threshold reference value.

The Capture Management algorithm is periodically run, e.g., once a day at a prescribed time to perform a pacing threshold search (PTS) wherein the pacing pulse amplitudes and pulse widths of the pacing pulses delivered in each pacing channel are incrementally adjusted within a predetermined range to determine the pacing threshold, and the threshold data is stored for analysis of long term trends. When an "Adaptive" mode of the Capture Management algorithm is programmed the Capture Management algorithm automatically adjusts the pacing pulse amplitude and/or pulse width setting to ensure capture at minimum pacing energy while maintaining the programmed safety margin(s).

A wide variety of other approaches have been taken as reflected by the extensive listing of earlier patents described in the above-referenced '310 patent and in commonly assigned U.S. Pat. Nos. 5,320,643, 5,324,310, 5,331,966, 5,601,615, 5,683,431, 5,861,012, 5,861,013, and 6,231,607, for example, and in further U.S. Pat. Nos. 4,686,988, 5,165,404, 5,165,405, 5,172,690, 5,222,493, 5,285,780, 5,564,430, and 5,683,426, for example.

The '310 patent, for example, discloses employing additional capture detection sense amplifiers and sense electrode pairs to detect the evoked response within an anticipated time following delivery of an A-PACE or V-PACE pulse. In other approaches, as exemplified by the above referenced '643 patent, one or more physiologic sensors that show a response to the mechanical action of the heart, e.g. a piezoelectric or impedance sensor, or that show changes in physical properties of the blood when the heart is captured, e.g. blood pH, temperature, impedance or blood pressure sensors on the pacing lead have also been suggested. In virtually all of these approaches, it is necessary to rely on additional components and circuitry that consume more energy and add to the bulk and cost of the system and raise reliability issues.

In one atrial auto-capture approach disclosed in U.S. Pat. No. 5,476,486, for example, the amplitudes of a series of A-PACE pulses are progressively decremented, and the presence or absence of a V-EVENT within an AV delay is noted. The absence of a V-EVENT indicates ALOC.

In one embodiment of the above-referenced '615 and '012 patents particularly for use with patients having intact and regular A-V conduction and with or without an intrinsic atrial sinus rhythm, A-PACE pulses are delivered at a test escape interval (that is shorter than any intrinsic atrial interval) and a paced AV (PAV) delay is timed out. An ALOC is declared in the absence of a detected V-EVENT in the latter portion of the test PAV delay following the delivery of the A-PACE test pulse. In the ventricular threshold test regimen, a V-PACE test pulse is delivered after a shortened test PAV delay timed from the preceding A-PACE pulse. A VLOC is declared by the detection of a V-EVENT in the ventricular refractory period of the delivered V-PACE pulse.

These atrial capture detection methods depend upon normal AV conduction, which is not present in many instances where the patient is pacemaker dependent in the ventricles. Therefore, these methods cannot be used if the patient has a high degree of AV block since an A-PACE triggered atrial depolarization is not conducted reliably to the ventricles to trigger a ventricular depolarization sensed as a V-EVENT.

In a second embodiment of the '615 and '012 patents, for use in the atrium or ventricle in patients having intrinsic sinus rhythm, each test A-PACE or V-PACE pulse is delivered at a test escape interval set as a fraction, e.g., about 50%–75% of the average intrinsic escape interval timed from a preceding A-EVENT or V-EVENT, respectively. A sense test window set to be somewhat longer than the test escape interval is timed out from delivery of the test A-PACE or V-PACE pulse. ALOC or VLOC is declared if an A-EVENT or V-EVENT, respectively, is detected within the sense test window. A-CAPTURE or V-CAPTURE is declared if an A-EVENT or V-EVENT, respectively, is detected after time-out of the sense test window. The energy of the test A-PACE pulse is successively incremented or decremented until an A-EVENT is detected within the sense test window, which signifies ALOC at the test energy of the previously delivered A-PACE test pulse. Preferably, in this embodiment, the test energy in pulse width and amplitude of the A-PACE or V-PACE test pulses is increased until A-CAPTURE or V-CAPTURE is declared so that the patient's normal rhythm is not disturbed frequently during the test.

These atrial and ventricular auto-capture methods depend upon the presence of normal sinus rhythm in the atrium and ventricles, respectively, which is not present in many instances where the patient is pacemaker dependent in one or both of the atria and the ventricles. In such a case, the sense test window cannot be determined since intrinsic A-EVENTs and V-EVENTs cannot be reliably detected.

Further auto-capture methods disclosed in U.S. Pat. Nos. 5,476,487, 5,674,254, and 6,216,037, rely upon the observation that the QT interval of the PQRST waveform varies in duration as a function of capture or LOC of the ventricles following a V-PACE or the atria following an A-PACE conducted to the ventricles. The commonly assigned '037 patent discloses an implantable DDD pacemaker incorporating a method for continually determining whether a delivered A-PACE pulse has resulted in capture of the atrium. A V-PACE is delivered after the time-out of a PAV delay, and the following QT interval is determined. An atrial depolarization that spontaneously occurs during the time-out of the PAV can affect the QT interval. The QT interval is measured on a cycle-by-cycle basis, stored, and employed in making a determination of change in QT interval, i.e., $)QT=*QT-QT_{PREV}*$. The )QT variable is compared to a lower limit, e.g., 2 ms, and a higher limit, e.g., 10 ms, and when )QT is within this range there is a determination of ALOC.

Detecting the QT interval following delivery of a V-PACE using the ventricular sense amplifier is itself difficult given the ventricular blanking and refractory intervals. Moreover, this approach presumes that the atria have an intrinsic depolarization rate that is overdriven at a faster atrial pacing rate. It also assumes that there is intact AV conduction, but that the ventricles are also paced. Typically, atrial and ventricular synchronized pacing is necessary during AV block and when the intrinsic atrial heart rate is lower than is desirable to provide sufficient cardiac output to meet the patient's needs.

What is needed in the art of determining ALOC is a capability of reliably detecting when a delivered A-PACE pulse has evoked an atrial depolarization without requiring special tests or additional components or circuitry that consume energy and add to the bulk and cost of the system. Specifically, there is a substantial need in a pacing system for an atrial capture detection method and system that function simply and reliably when the patient is pacemaker dependent in the atria or in both the atria and the ventricles.

SUMMARY OF THE INVENTION

In accordance with the present invention, simple and effective systems and methods for determining A-CAPTURE and ALOC are provided in AV synchronous, dual chamber, pacing systems or any atrial based pacing system.

In the atrial capture management (ACM) algorithms of the present invention, the A-PACE pulse energy, defined by the pulse width and pulse amplitude, is sufficient to reliably capture the atrium without being wasteful of battery energy is periodically determined. The ACM algorithms allow a slow intrinsic atrial heart rate that is suppressed by delivered A-PACE pulses resulting in A-CAPTURE and that occurs when delivered test A-PACE pulses result in ALOC to be detected. ALOC is declared if an A-EVENT of the slow intrinsic atrial heart rate is detected either during an ACM test window timed from the delivered test A-PACE pulse or during delivery of a sequence of test A-PACE pulses delivered within or defining the ACM test window. In particular embodiments, ALOC declaration is made when the slow intrinsic atrial heart rate is detected within the ACM test window in repeated delivery of the test A-PACE pulses and time-out of the ACM test window.

In certain embodiments, a series of test A-PACE pulses are delivered within the ACM test window, and ALOC is declared if a refractory or non-refractory A-EVENT occurs during the delivery of the test A-PACE pulses. In these embodiments, ventricular pacing and sensing can be provided during delivery of the test A-PACE pulses in a dual chamber pacing mode, e.g., a DDD pacing mode. The occurrence of a refractory or non-refractory A-EVENT signifies that the series of test A-PACE pulses have not resulted in A-CAPTURE, allowing the atria to depolarize at the slow intrinsic atrial heart rate, unless the A-EVENT is deemed to represent far field sensing of a ventricular depolarization or a retrograde conduction of a ventricular depolarization.

In a further embodiment, atrial and ventricular pacing is suppressed over the ACM test window by prolonging the A-A pacing escape interval from the last delivered test A-PACE pulse to time-out the ACM test window. Any A-EVENT detected during time out of the prolonged escape interval signifies that the test A-PACE pulse did not result in A-CAPTURE, allowing the atria to depolarize at the slow intrinsic atrial heart rate, unless the A-EVENT is deemed to represent far field sensing of a ventricular depolarization or a retrograde conduction of a ventricular depolarization.

The sensed refractory or non-refractory A-EVENT is deemed to represent far field sensing of a ventricular depolarization V-EVENT or a retrograde conduction of a ventricular depolarization if the A-EVENT closely follows (within a defined window) a V-EVENT or a delivered V-PACE. Preferably, an abort count is incremented in that case, and the ACM algorithm is aborted if repeated sensing of retrograde conducted V-EVENTs or far field sensing of V-EVENTs occurs.

Advantageously, it is fairly simple to determine that a patient has a slow atrial rhythm from ECG or EGM tracings and during testing at implantation and at follow-ups. Further, the present method may work in patients in whom the methods in the prior art may fail because, for example, the patient did not have the stable AV conduction needed for one method, or because the patient was paced at too high a rate for another method to be effectively used.

The ACM algorithms of the present invention can be programmed ON or OFF by the physician responsible for the patient.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention.

Figure 1:
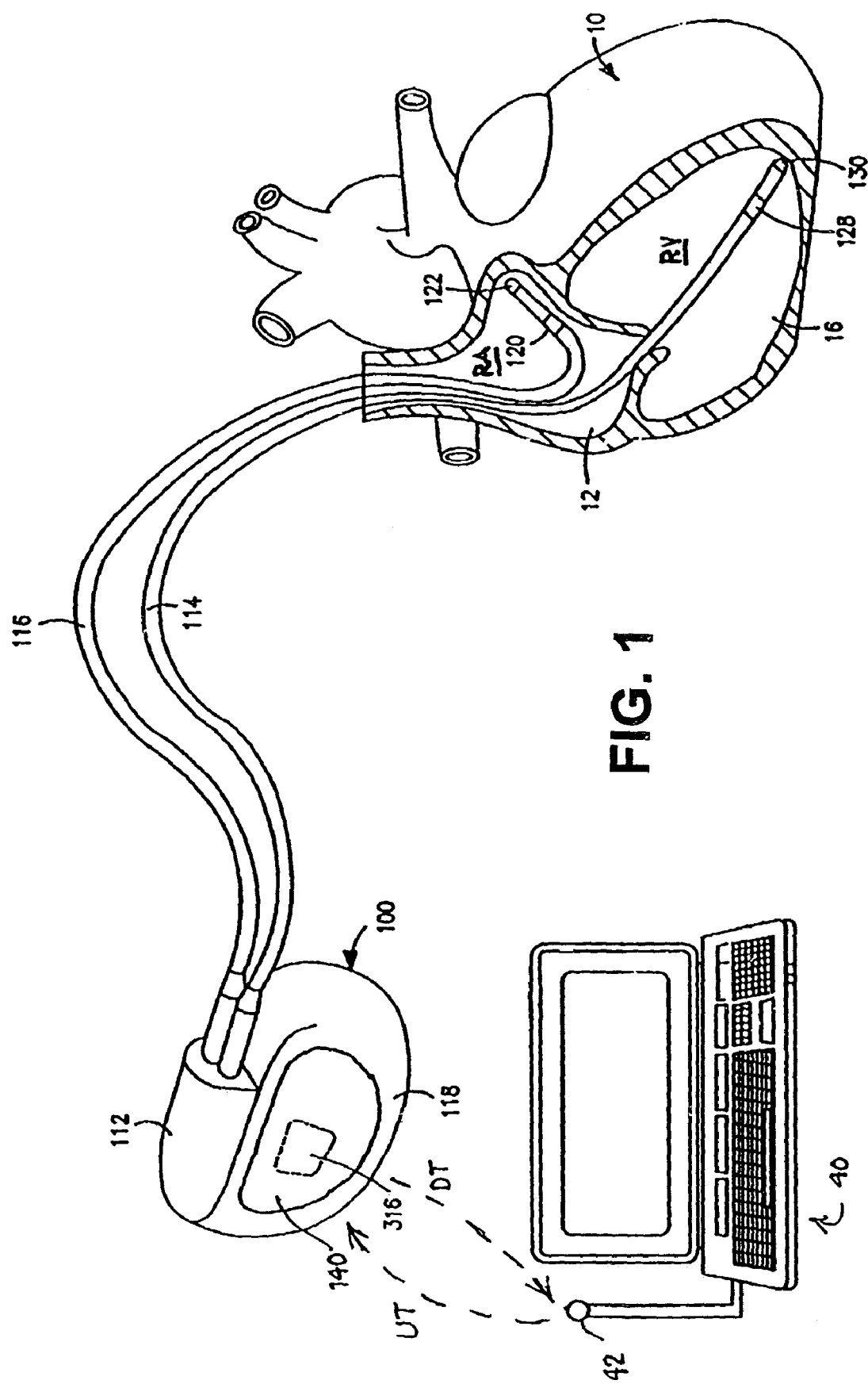
FIG. 1 is a schematic illustration of a dual chamber pacemaker implanted in a patient's chest comprising an IPG and endocardial leads transvenously introduced into the right atrium and right ventricle of the heart.
Figure 2:
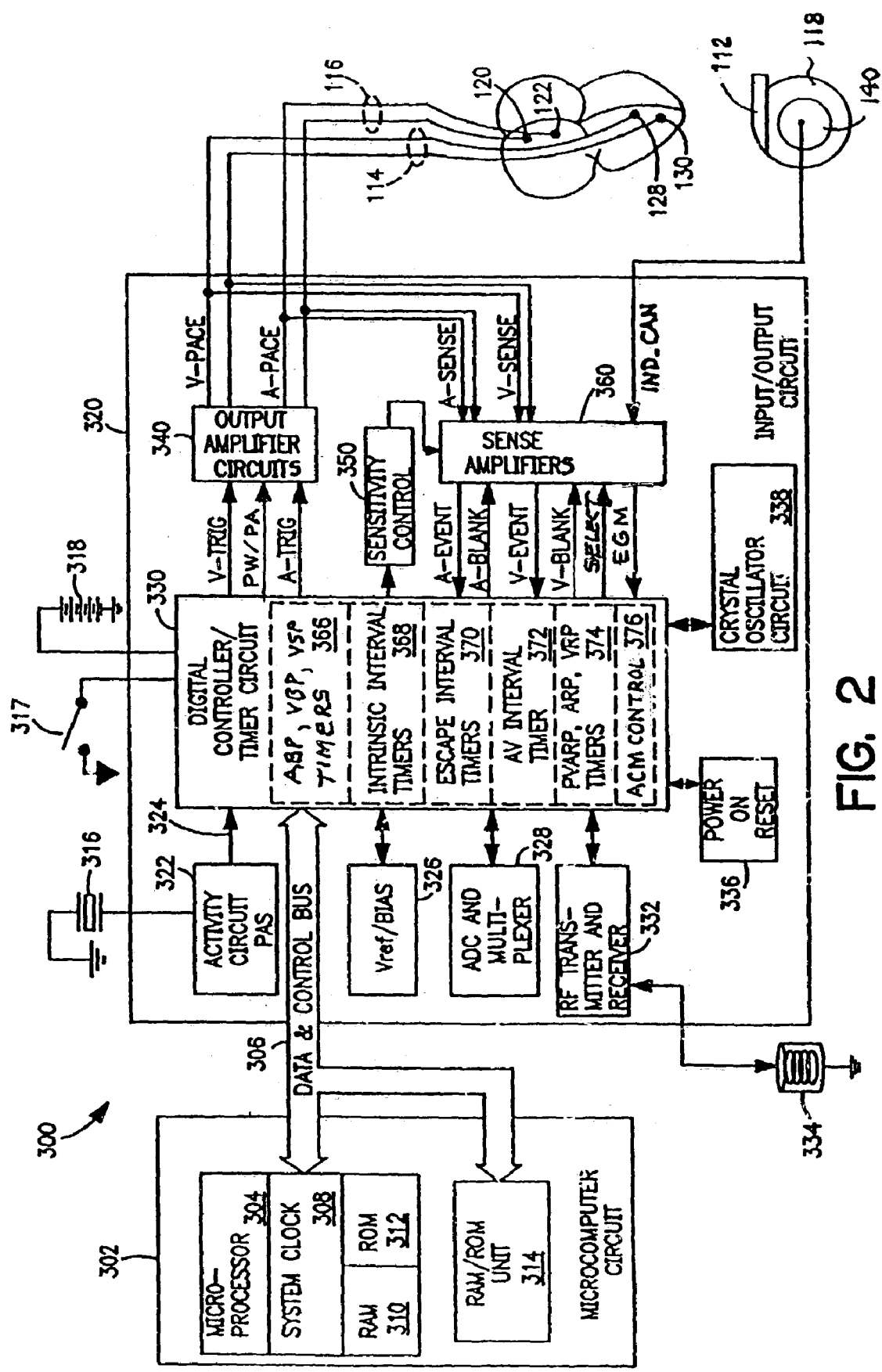
FIG. 2 is a block diagram of the pacing IPG of FIG. 1 in which the present invention may be practiced.

The present invention can be implemented in a dual chamber pacing system that is incorporated into a dual chamber pacemaker, a multi-chamber pacemaker providing right and left atrial and ventricular pacing, or an ICD or other IMD incorporating such pacing systems. The following description of a dual chamber pacemaker is thus intended to encompass all of the various types of dual chamber pacing systems in which the present invention can be implemented. FIGS. 1 and 2 therefore depict the external configuration and components of a typical implantable dual chamber pacemaker typically operating in a DDD, DDI, DDIR, or DDDR pacing mode but capable of operating in other pacing modes under prescribed conditions as described further herein.

Such a dual chamber IPG 100 and unipolar or bipolar atrial and ventricular leads 114 and 116 (bipolar leads are depicted), in which the present invention may be implemented is depicted in FIGS. 1 and 2. The dual chamber IPG 100 of FIG. 1 is also shown in relation to an external programmer 40 and external programmer telemetry antenna 42 providing uplink telemetry (UT) and downlink telemetry (DT) transmissions with an IPG antenna. The programming of IPG operating modes and parameters or the interrogation of data stored in the IPG 100 or the initiation of UT transmission of the real time cardiac EGM is accomplished or initiated via programming or interrogation commands transmitted in a DT transmission by programmer 40 from the external telemetry antenna 42 to an IPG telemetry antenna 334 shown in FIG. 2. The IPG telemetry system decodes the commands in the DT transmission, retrieves and formats the responsive data or cardiac EGM and conveys it to the external programmer 40 as an UT transmission in any of the manners known in the art. In the context of the present invention, the ICD operating system stores ACM data that can be UT transmitted to the external programmer 40 for review by a physician.

Figure 3:
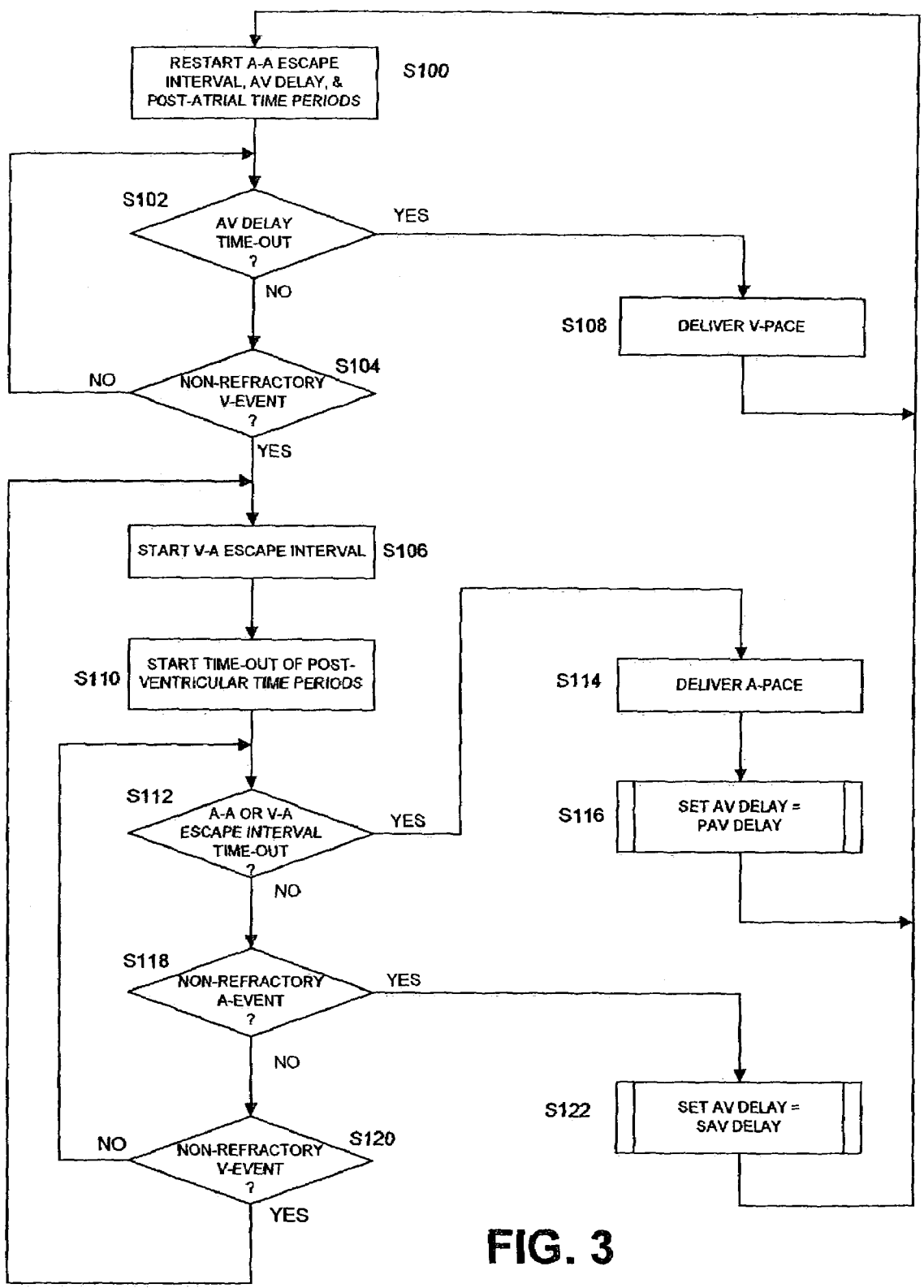
FIG. 3 is flow chart depicting the steps of a DDD/DDDR pacing cycle.

The dual chamber pacemaker IPG 100 senses and paces in the atrial and ventricular chambers, and pacing is either triggered and inhibited depending upon sensing of intrinsic, non-refractory atrial and ventricular depolarizations during the sequentially timed A-A escape interval and AV delay, respectively, as is well known in the art, in accordance with the steps set forth in the flow chart of FIG. 3. In the typical dual chamber DDD pacing system, an A-PACE pulse generated by the atrial pace pulse generator is applied to the right atrial active and indifferent pace/sense electrodes to cause the right and left atria to depolarize. Similarly, a V-PACE pulse generated by the ventricular pulse generator is applied to the right ventricular active and indifferent pace/sense electrodes to cause the right and left ventricles to depolarize. The present invention functions periodically in accordance with an ACM algorithm to determine the A-PACE energy, defined by the pulse width and pulse amplitude, sufficient to reliably capture the atrium without being wasteful of battery energy.

The IPG 100 is provided with a hermetically sealed enclosure or can 118, typically fabricated of biocompatible metal such as titanium, enclosing the dual chamber IPG circuit 300 depicted in FIG. 2. A connector block assembly 112 is mounted to the top of the can 118 to receive electrical connectors located on the proximal connector ends of the depicted bipolar atrial and ventricular pacing leads 114 and 116.

An electrically exposed area of the can 118 can also function as an IND_CAN electrode 140 that is electrically connected to one input of a far field sense amplifier to facilitate sensing of the atrial and/or ventricular EGM for storage and analysis in various ways known in the art. It is also possible to program an indifferent electrode selection to use the IPG 100 IND_CAN electrode 140 is as an indifferent pace/sense electrode for unipolar atrial and/or ventricular pacing.

The bipolar atrial pacing lead 116 extends between its proximal connector coupled to IPG 100 and distal atrial pace/sense electrodes 120 and 122 located in the right atrium 12 of heart 10 to enable sensing of P-waves and delivery of atrial pacing pulses to the right atria. A-PACE pulses may be delivered between atrial pace/sense electrodes 120 and 122 in a bipolar pacing mode or between atrial pace/sense electrode 122 and the IND_CAN electrode 140 of the IPG 100 in a unipolar pacing mode. Sensing of P-waves by the atrial sense amplifier may occur between atrial pace/sense electrodes 120 and 122 in a bipolar sensing mode or between either of atrial pace/sense electrode 120 and 122 and the IND_CAN electrode 140 of the IPG 100 in a unipolar atrial sensing mode.

Similarly, the bipolar ventricular pacing lead 114 extends between its proximal connector coupled to IPG 100 and distal ventricular pace/sense electrodes 128 and 130 located in the right ventricle 16 of heart 10 to both sense R-waves and to deliver ventricular pacing pulses to the ventricles. V-PACE pulses may be delivered between ventricular pace/sense electrodes 128 and 130 in a bipolar pacing mode or between ventricular pace/sense electrode 130 and the IND_CAN electrode 140 of the IPG 100 in a unipolar pacing mode. Sensing of R-waves by the ventricular sense amplifier occurs between ventricular pace/sense electrodes 128 and 130 in a bipolar sensing mode or between either of ventricular pace/sense electrode 128 and 130 and the IND_CAN electrode 140 of the IPG 100 in a unipolar ventricular sensing mode.

The IPG circuit 300 within IPG 100 and the bipolar atrial and ventricular leads 114 and 116 are depicted in FIG. 2 in relation to heart 10. The IPG circuit 300 is divided generally into a microcomputer circuit 302 and a pacing input/output circuit 320. The input/output circuit 320 includes the digital controller/timer circuit 330, the atrial and ventricular pacing pulse output circuit 340 and the atrial and ventricular sense amplifiers circuit 360, as well as a number of other components and circuits described below. The digital controller/timer circuit 330 provides control of timing and other functions within the input/output circuit 320. Digital controller/timer circuit 330, operating under the general control of the microcomputer circuit 302, includes a set of timing and associated logic circuits, of which certain ones pertinent to the present invention are depicted and described further below. The pacing operating system times out an A-A escape interval (in DDD and DDDR modes) or a V-V interval (in VDD and VDDR modes) upon a V-EVENT or V-PACE pulse and times out an AV delay in response to an A-EVENT (in VDD, VDDR, DDD, DDDR modes) or in response to an A-PACE pulse (in DDD and DDDR modes) as well as a number of other intervals. An SAV delay is commenced by declaration of an A-EVENT, and a PAV delay is commenced upon delivery of the A-PACE pulse in certain DDD and DDDR pacing systems.

The depicted counters and timers within digital controller/timer circuit 330 include ABP and VBP timers 366, intrinsic interval timers 368 for timing average intrinsic A-A and V-V intervals from A-EVENTs and V-EVENTs, escape interval timers 370 for timing A-A, V-A, and/or V-V pacing escape intervals, an AV delay timer 372 for timing the SAV delay from a preceding A-EVENT or PAV delay from a preceding A-TRIG, refractory period timers 374 for timing ARP, PVARP and VRP times, and an ACM controller 376 for controlling performance of the ACM functions of the present invention. Digital controller/timer circuit 330 starts and times out these intervals and time periods that are calculated by microcomputer circuit 302 for controlling the above-described operations of the atrial and ventricular sense amplifiers in sense amplifiers circuit 360 and the atrial and ventricular pace pulse generators in output amplifier circuit 340.

Preferably, the IPG 100 or one of the leads 114 or 116 includes one or more physiologic sensor that develops a physiologic signal that relates to the need for cardiac output. The use of physiologic sensors to provide variation of pacing rate in response to sensed physiologic parameters, such as physical activity, oxygen saturation, blood pressure and respiration, has become commonplace. The rate-adaptive VDDR, DDIR, and DDDR pacing modes function in the above-described manner but additionally provide rate modulation of a pacing escape interval between a programmable lower rate and an upper rate limit (URL) as a function of a physiologic signal or rate control parameter (RCP) related to the need for cardiac output developed by a physiologic sensor. At times when the intrinsic atrial rate is inappropriately high or low, a variety of "mode switching" schemes for effecting switching between tracking modes and non-tracking modes (and a variety of transitional modes) based on the relationship between the atrial rate and the sensor derived pacing rate have been proposed as exemplified by commonly assigned U.S. Pat. No. 5,144,949.

Commonly assigned U.S. Pat. Nos. 4,428,378 and 4,890,617 disclose activity sensors that are employed to vary the pacing escape interval in single and dual chamber pacemaker IPGs in response to sensed physical activity. Such an activity sensor 316 is coupled to the inside surface of the IPG hermetically sealed enclosure 118 and may take the form of a piezoelectric crystal transducer as is well known in the art. The activity sensor 316 generates an output signal in response to certain patient activities, e.g. ambulating, that is processed and used as the RCP. If the IPG operating mode is programmed to a rate responsive mode, the patient's activity level developed in the patient activity circuit (PAS) 322 is monitored, and a sensor derived V-A, A-A or V-V escape interval is derived proportionally thereto. A timed interrupt, e.g., every two seconds, may be provided in order to allow the microprocessor 304 to analyze the output of the activity circuit PAS 322 and update the basic V-A (or A-A or V-V) escape interval employed to govern the pacing cycle and to adjust other time intervals as described below.

The bipolar leads 114 and 116 are illustrated schematically with their associated pace/sense electrode sets 120, 122 and 128, 130, respectively, as coupled directly to the atrial and ventricular pacing pulse output circuit 340 and sense amplifiers circuit 360 of pacing circuit 320. The atrial and ventricular pacing pulse output circuit 340 and sense amplifiers circuit 360 contain pulse generators and sense amplifiers corresponding to any of those presently employed in commercially marketed cardiac pacemakers for atrial and ventricular pacing and sensing.

In order to trigger generation of a V-PACE pulse, digital controller/timer circuit 330 generates a V-TRIG signal at the end of a PAV or SAV delay provided by AV delay timer 372. Similarly, in order to trigger an atrial pacing or A-PACE pulse, digital controller/timer circuit 330 generates an A-TRIG signal at the termination of the A-A escape interval timed out by escape interval timers 370. The pulse width (PW) and pulse amplitude (PA) of the A-PACE pulse and V-PACE pulse width is defined by PA and PW signals that are either the prevailing programmed PA and PW or are periodically determined in an ACM algorithm. The A-PACE and V-PACE pulses are produced by the exponential discharge of respective atrial and ventricular output capacitors through the impedance loads in the atrial and ventricular pacing paths that each include a coupling capacitor, the active and indifferent pace/sense electrodes, and the patient's heart tissue between the pace/sense electrodes.

Sense amplifiers circuit 360 includes atrial and ventricular sense amplifiers of the types disclosed for example, in the above-referenced '013 patent. Sense amplifiers circuit 360 also comprises a far field sense amplifier coupled with the IND_CAN electrode 140 and one of the ventricular pace/sense electrodes 128 or 130 selected by a SELECT signal so that a far field atrial and/or ventricular EGM can be sensed along a bipolar or far-field sense vector.

Sensitivity settings of the atrial and ventricular sense amplifiers and the EGM sense amplifier in sense amplifiers circuit 360 can be programmed by the physician to reliably sense true P-waves, R-waves and premature ventricular contractions (PVCs) during a patient work-up at implantation or during a patient follow-up telemetry session so that true A-EVENT and V-EVENT signals are generated. Digital controller/timer circuit 330 controls the sensitivity settings of the atrial and ventricular sense amplifiers in sense amplifiers circuit 360 by means of sensitivity control 350.

It is conventional to suppress or blank both of the atrial and ventricular sense amplifiers during A-PACE and V-PACE pulses for blanking periods to avoid overloading the sense amplifier. Moreover, the sense amplifiers may abruptly sense a different potential than was present at the time of initial blanking when the blanking period expires and the sense amplifier is reconnected due to the afterpotentials and electrode polarization as well as the recharge function. This can produce unwanted oversensing of artifacts resulting in false declarations of A-EVENTs or V-EVENTs. Therefore, the blanking periods in pacemaker IPGs sold by the assignee of this application are nominally set at 30 ms after delivery of an A-PACE or V-PACE, but the blanking periods may be programmed as long as 45 ms in difficult sensing scenarios. There may be additional digital blanking of the sense amplifiers to avoid sensing of evoked response or other pacing artifacts, e.g., for 150 ms to 400 ms after paced events in ICDs.

Accordingly, ABP and VBP timers in block 366 of digital controller/timer circuit 330 time out an atrial blanking periods (ABP) including a post A-PACE, atrial blanking period (PAABP or PAAB) and a post V-PACE, atrial blanking period (PVABP or PVAB) or as a ventricular blanking periods (VBP) including a post A-PACE, ventricular blanking period (PAVBP or PAVB), and a post V-PACE, ventricular blanking period (PVVBP or PVB). Thus, the appropriate atrial blanking (A-BLANK) signal is applied to the atrial sense amplifier for the prevailing ABP, and a ventricular blanking (V-BLANK) signal is applied to the ventricular sense amplifier for the prevailing VBP. In the absence of an A-BLANK signal, atrial depolarizations or P-waves that are detected by the atrial sense amplifier result in an A-EVENT that is communicated to the digital controller/timer circuit 330. Similarly, in the absence of a V-BLANK signal, ventricular depolarizations or R-waves that are detected by the ventricular sense amplifier result in a V-EVENT that is communicated to the digital controller/timer circuit 330.

As noted above, after-potentials on the ventricular pace/sense electrodes at time-out of the PAVBP can erroneously be detected and result in declaration of a V-EVENT by the ventricular sense amplifier. The pacing system will not provide appropriate ventricular pacing to a patient's heart having AV block if electrical noise or other signals are mistakenly sensed by the ventricular sense amplifier as V-EVENTs during time-out of the AV delay. The questionable nature and consequences of mistakenly detecting V-EVENTs has led to the adoption of the practice of delivering a ventricular safety pace (VSP) pulse at a fixed time, typically 110 ms, following delivery of an A-PACE. In other words, a VSP pulse is delivered to the ventricular pace/sense electrodes if a V-EVENT is declared between the time-out of the PAVBP and a 110 ms VSP window following delivery of an A-PACE pulse. This 110 ms VSP window is often denoted the cross talk window. The 110 ms VSP window length is shorter than the normal AV conduction time in humans, so any V-EVENT declared within the VSP window is unlikely to be due to true AV conduction. The delivered VSP pulse captures the ventricles if the V-EVENT was due to cross talk, that is, sensing of the residual A-PACE energy after-potentials. The delivered VSP pulse will not capture the ventricles if the V-EVENT reflects a PVC, because the ventricles will be refractory at that time. Thus, faced with this uncertainty, a VSP pulse is delivered at time-out of the VSP window or delay so as to ensure that the ventricles are truly contracting at a safe time after delivery of the A-PACE pulse. The VSP window is timed out by a VSP timer in block 366 of digital controller/timer circuit 330.

In addition, a number of sense amplifier refractory periods are timed out on A-EVENT and V-EVENT signals and generation of A-PACE and V-PACE pulses, whereby "refractory" A-EVENT and V-EVENTs during such refractory periods are selectively ignored or employed in a variety of ways to reset or extend time periods being timed out. The refractory period timers 374 time out atrial and ventricular refractory periods (ARP and VRP) commenced upon an A-EVENT or V-EVENT or generation of an A-PACE or V-PACE pulse, respectively. The ARP is typically only employed by itself during atrial demand pacing in the AAI pacing mode. In dual chamber pacing modes, the ARP commenced by the A-EVENT or A-PACE pulse extends through the SAV delay or the PAV delay until a certain time following a V-EVENT terminating the SAV or PAV delay or generation of a V-PACE pulse at the expiration of the SAV or PAV delay. This post-ventricular atrial refractory period (PVARP) is commenced by a V-PACE pulse or V-EVENT based on the understanding that A-EVENTs sensed during its time-out generally reflect a retrograde conduction of the evoked or spontaneous ventricular depolarization wave and therefore are not employed to reset an escape interval and commence an SAV delay. The duration of PVARP may be fixed or vary as a function of sensed atrial rate or pacemaker defined pacing rate, with the result that in many cases relatively long PVARPs are in effect at lower rates. A total ARP (TARP) is defined as the entire duration of the ARP and the PVARP.

An A-EVENT is characterized as a refractory A-EVENT (AR-EVENT in the following) if it occurs during time-out of an ARP or a PVARP or a non-refractory A-EVENT if it occurs after time-out of these atrial refractory periods. Similarly, a V-EVENT is characterized as a refractory V-EVENT (VR-EVENT in the following) if it occurs during time-out of a VRP or a non-refractory V-EVENT if it occurs after time-out of the ventricular refractory period. AR-EVENTs and VR-EVENTs are typically ignored for purposes of resetting timed out AV delays and A-A escape intervals, although diagnostic data may be accumulated related to their occurrences. However, in accordance with the ACM algorithms of the present invention an AR-EVENT detected during the ACM test window is treated the same as an A-EVENT to signify ALOC as described further below.

Microcomputer 202 contains a microprocessor 304 and associated system clock 308 and on-processor RAM and ROM chips 310 and 312, respectively. In addition, microcomputer circuit 302 includes a separate RAM/ROM chip 314 to provide firmware and additional RAM memory capacity. Microprocessor 304 is interrupt driven, operating in a reduced power consumption mode normally, and awakened in response to defined interrupt events, which may include the A-TRIG, V-TRIG, A-EVENT and V-EVENTs.

Microcomputer 302 controls the operational functions of digital controller/timer 324, specifying which timing intervals are employed in a programmed pacing mode via data and control bus 306. The specific values of the intervals timed by the digital controller/timer circuit 330 are controlled by the microcomputer circuit 302 by means of data and control bus 306 from programmed-in parameter values. The microcomputer 302 also calculates the RCP derived or intrinsic atrial rate derived V-V, A-A or A-A escape interval, the variable AV delay, and the variable ARP, PVARP and VRP. Typically, the AV delay in modern VDD, VDDR, DDD and DDDR pacemakers is either fixed or varies with the prevailing intrinsic atrial rate, measured as an A-A interval, and/or varies as a function of a physiologic sensor derived pacing rate.

Digital controller/timer circuit 330 also interfaces with other circuits of the input output circuit 320 or other components of IPG circuit 300. Crystal oscillator circuit 338 provides the basic timing clock and battery 318 provides power for the pacing circuit 320 and the microcomputer circuit 302. Power-on-reset circuit 336 responds to initial connection of the circuit to the battery 318 for defining an initial operating condition and similarly, resets the operative state of the IPG circuit 300 in response to detection of a low battery condition. Reference mode circuit 326 generates stable voltage reference and currents for the analog circuits within the pacing circuit 320. ADC (analog to digital converter) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

Data transmission to and from an external programmer (not shown) during a telemetry session is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Reed switch 317 when closed by application of a magnetic field may be employed to enable programming of the pacemaker and also may be employed to convert the pacemaker temporarily to an asynchronous pacing mode such as DOO or VOO. Operation in the asynchronous mode may continue as long as the magnetic field is present, may continue until overridden by the programmer or may continue for a pre-set time period.

The illustrated IPG circuit 300 of FIG. 2 is merely exemplary, and corresponds to the general functional organization of most multi-programmable microprocessor controlled DDD and DDDR cardiac pacemaker IPGs presently commercially available. It is believed that the ACM algorithms of the present invention can readily be practiced using combinations of hardware, firmware, and software of existing microprocessor controlled, dual chamber pacing systems that are incorporated into dual chamber pacemakers or into ICDs or into right and left heart pacing systems. The operating functions of the ACM algorithms of the present invention may also be usefully practiced by means of a full custom integrated circuit, for example, a circuit taking the form of a state machine, in which a state counter serves to control an arithmetic logic unit to perform calculations according to a prescribed sequence of counter controlled steps.

FIG. 3 is a functional flow chart of a typical overall pacing cycle timing operation of the pacemaker IPG circuit 300 illustrated in FIG. 2 in the DDD or DDDR pacing modes. In the flow chart of FIG. 3, it is assumed that the A-A or V-V escape interval, cardiac cycle timing of the IPG circuit 300 ranges between a programmed lower rate and a programmed URL and is based on the definition of a prevailing A-A escape interval and an AV delay, specifically either the SAV or the PAV delay interval. The AV delay and A-A escape interval of any given pacing cycle may be determined as a function of a sensor-derived A-A escape interval or an atrial rate based A-A escape interval determined by the average measured intrinsic A-A atrial rate if it is stable and varies between the programmed lower rate and URL. In this particular embodiment, separate SAV and PAV delays are defined, although in practice they may have the same duration. The operations of the flow chart may also incorporate any of the mode switching and sinus preference algorithms of the prior art described above to switch between the use of the sensor or the atrial rate derived escape intervals. However the overall pacing cycle timing operation is specifically implemented, it is understood to incorporate the ACM algorithms of the present invention as described hereafter.

For convenience, the pacing cycle is assumed to begin at step S100 starting from a non-refractory A-EVENT sensed in step S118. Timing of the prevailing SAV delay set in step S122 and the post A-EVENT time periods described above are commenced in step S100. The operating system awaits either time out of the SAV delay in step S102 or a non-refractory V-EVENT in step S104. A V-PACE is delivered in step S108 upon time-out of the SAV delay without a V-EVENT declared in step S104. The SAV delay is terminated without delivery of a V-PACE pulse if a V-EVENT is declared in step S104.

In either case, the A-A escape interval time-out is commenced in step S108, and time-out of the post ventricular time periods including the VRP, PVARP, PAVBP and PVVBP are commenced in step S110. The algorithm awaits expiration of the A-A escape interval at step S112, and it is possible that a refractory or non-refractory A-EVENT or V-EVENT can occur during the A-A escape interval time-out.

The A-A escape interval is terminated if a non-refractory A-EVENT is sensed in step S118 during time-out the A-A escape interval. The AV delay is set to the SAV delay in step S122, and the SAV delay and associated post atrial sense ARP is timed out in step S100. Optionally, the non-refractory A-EVENT also causes the A-A escape interval to be measured by intrinsic interval timer 368 and employed to derive or update an intrinsic atrial rate that is saved in RAM. The A-A escape interval, the SAV and PAV delays, the PVARP, and the pacing escape interval for the next cardiac cycle can then be recalculated in dependence upon either the updated average A-A interval or upon the RCP in a manner well known in the art. For convenience, the A-A escape interval that is determined and timed out over the period between successive performances of the ACM algorithm is referred to as the "prevailing A-A escape interval" herein.

If a non-refractory V-EVENT is declared sensed by the ventricular sense amplifier at step S120 during time out of the A-A escape interval in the absence of detection of a preceding A-EVENT, then the declared V-EVENT is characterized as a PVC. The time-out of the prevailing A-A escape interval is halted in response to the PVC, and time-out of a V-A escape interval in step S106 and the post-ventricular time periods in step S110 are commenced. Certain algorithms, e.g., those disclosed in commonly assigned U.S. Pat. No. 6,311,088, have been devised to deal with such PVCs occurring during the A-A escape interval that could be practiced along with but are not necessary to the practice of the present invention.

An A-TRIG signal is generated leading to delivery of an A-PACE pulse in step S114 at the time-out of the A-A escape interval if the A-A escape interval times out without sensing any such intervening non-refractory A-EVENT or V-EVENT. In this case, the next succeeding AV delay is defined to be equal to PAV at step S116, and the PAV and post A-PACE time periods described above are timed out in step S100. The operating system awaits either time out of the PAV delay in step S102 or a non-refractory V-EVENT in step S104.

Various embodiments of the ACM algorithm of the present invention are set forth in FIGS. 4 through 9. In step S200 of FIG. 4, step S300 of FIG. 5, and step S400 of FIG. 6, the pacing system functions in the normal mode of FIG. 3 as described above. The physician programs a set of ACM test criteria that must be met in steps S202, S302 and S402 before the ACM algorithm can be commenced. The physician typically schedules the ACM algorithm to operate once a day at a time of day when the patient is expected to be at rest, e.g., at night while the patient is expected to be asleep. Moreover, the physician may program or the algorithm may be preset to only commence if the patient's intrinsic atrial and/or ventricular heart rate is below a certain rate limit, e.g., 100 bpm, and/or the output of the PAS circuit 322 signifies that the patient is at rest. In addition, the ACM algorithm cannot commence if competing operations of the pacing IPG are functioning, such as mode switching or rate drop response, among others in a manner described in the Kappa® 900/800 *Series Pacemaker Reference Guide*, for example, or if the physician programs it OFF.

The various embodiments of the ACM algorithms of the present invention typically function when the patient is paced in the atrium. The patient's heart could, for example, be chronoptropically incompetent, such that the prevailing A-A escape interval is being set as a function of the output of the PAS circuit 322 or when the patient's intrinsic atrial heart rate as evidenced by the interval or cycle length between successive A-EVENTS falls below the pacing lower rate, which is typically programmed at about 1000 ms (60 bpm). Such patients may have an underlying sinus atrial rate of 25–60 bpm, for example, that is suppressed by the delivered A-PACE pulses as long as A-CAPTURE results. Moreover, the ACM algorithms of the present invention function when the patient is in AV block. As noted above, it is fairly simple to determine that the atria do or do not have an underlying slow intrinsic rate. Furthermore, the ACM algorithms of the present invention function when the patient's rhythm and rate would otherwise appear to be suited to algorithms of other methods, such as those that require stable AV conduction or that require stable intrinsic atrial sensing intervals, since the patient may have, for example, stable atrial sensing but at a rate may be too high for alternative methods, or AV conduction but at intervals too variable for alternative methods.

Thus, in step S204, the alternative methods, e.g., the capture management methods described in the above-referenced patent application Ser. Nos. 10/004,164 and 10/434,689, are performed. Normal pacing is resumed in step S200 of it is possible to successfully use those alternative algorithms of step S204 to determine ALOC and set the new prevailing A-PACE energy as determined in step S206. Steps S208 of the ACM algorithm of the present invention are followed if it is not possible to successfully use those alternative algorithms of step S204 to determine ALOC and set the new prevailing A-PACE energy as determined in step S206.

These steps S202–S206 (and corresponding steps S302–S306 of FIG. 6 and S402–S406 of FIG. 8) are merely exemplary of possible threshold steps preceding the start of the remaining ACM steps S208–S226. Consequently, steps S202–S206, S302–S306 and S402–S406 can be selectively eliminated or altered in any way considered appropriate.

For example, under certain conditions, A-PACE and V-PACE pulses may be repetitively delivered in steps S108 and S114, respectively, of FIG. 3 as the prevailing A-A escape interval or V-A escape interval times out in step S106 and the PAV delay times out in step S100. An A-PACE and V-PACE history over a period of minutes, hours, or longer could be maintained in RAM registers and checked in step S202, S302, S402 to determine the degree of atrial and ventricular pacing dependency. If a requisite degree of atrial and ventricular pacing dependency were present, then the ACM algorithms of the present invention could be performed without first performing the alternative capture management algorithms in step S204, S304, S404.

In each of the ACM algorithms of the present invention, steps S210–S228, S310–S328, and S410–S428 are repeated a number of times to determine one or both of the test A-PACE pulse width and pulse amplitude at ALOC. When both A-PACE pulse width and pulse amplitude at ALOC are determined the test A-PACE pulse energy is automatically incremented or decremented depending on where the ACM algorithm is in its total cycle. Since it is necessary to perform the rheobase test first, the pacing pulse amplitude is decremented at a given test A-PACE pulse width. For example, the test A-PACE pulse width can be set at 0.4 ms, and the A-PACE pulse amplitude can be decreased incrementally at this pulse width, and the steps repeated, until ALOC occurs. Then, the test A-PACE pulse amplitude can be increased incrementally, and the steps repeated until A-CAPTURE is regained. The test A-PACE pulse amplitude at which capture is regained (the "rheobase" threshold) is used as a benchmark A-PACE pulse amplitude to use during the chronaxie test for ALOC and recapture. The test A-PACE pulse amplitude is doubled from the rheobase while the test A-PACE pulse width is decremented to lose capture and incremented to regain A-CAPTURE. Thus, the pulse width is decreased from a known value until LOC occurs, and then increased until capture is again attained to determine the "chronaxie" threshold.

However, it is sufficient to determine only one of the test A-PACE pulse width or pulse amplitude at ALOC and to use that test A-PACE pulse width or pulse amplitude to set the A-PACE pulse energy. Therefore, the depicted steps S208–S226 show the determination of only one of the test A-PACE pulse width or pulse amplitude at ALOC. Generally, the determination of a test A-PACE pulse width or pulse amplitude at ALOC is repeated a number of times, e.g., 2 out of 3 successive times, to increase assurance that it has been accurately determined.

The ACM algorithms of the present invention allow a slow intrinsic atrial heart rate that occurs when delivered test A-PACE pulses result in ALOC to be detected. The slow intrinsic atrial heart rate is normally suppressed by delivered A-PACE pulses resulting in A-CAPTURE. ALOC is declared if an A-EVENT of the slow intrinsic atrial heart rate is detected either during an ACM test window timed from the last delivered test A-PACE pulse or during delivery of a sequence of test A-PACE pulses delivered within or defining the ACM test window.

Figure 4:
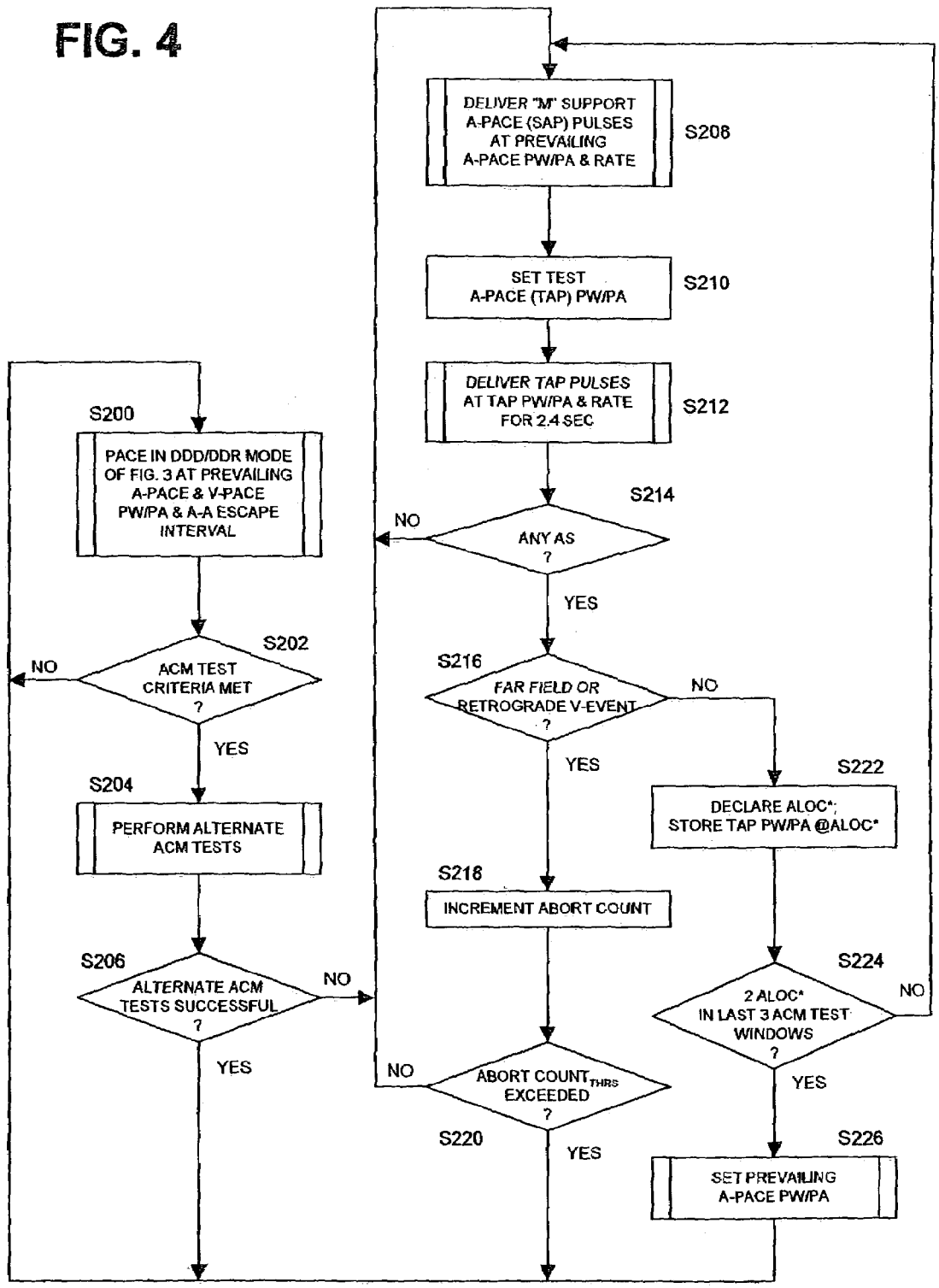
FIG. 4 is a detailed flow chart depicting one embodiment of an ACM algorithm of the present invention.
Figure 5:
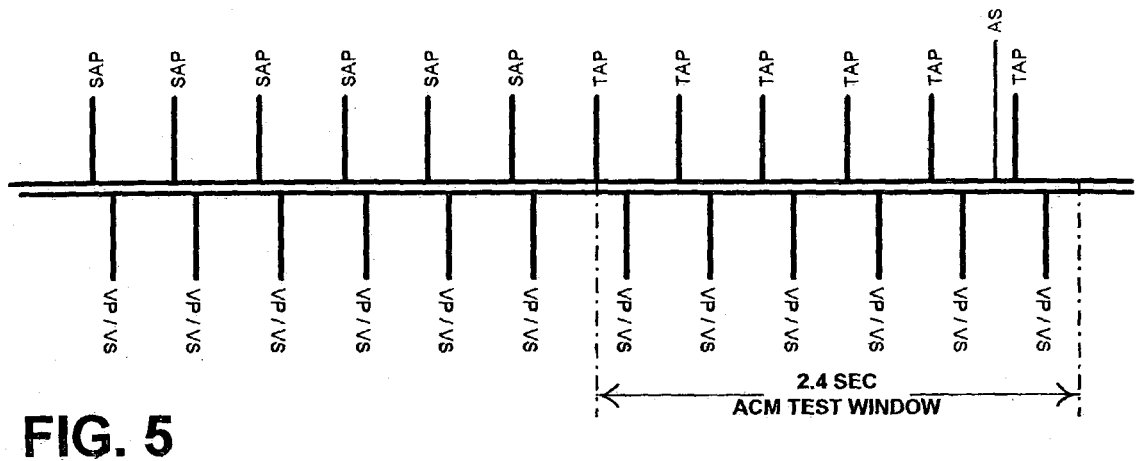
FIG. 5 is a tracing of atrial and ventricular pace and sense events illustrating the ACM algorithm of FIG. 4.
Figure 7:
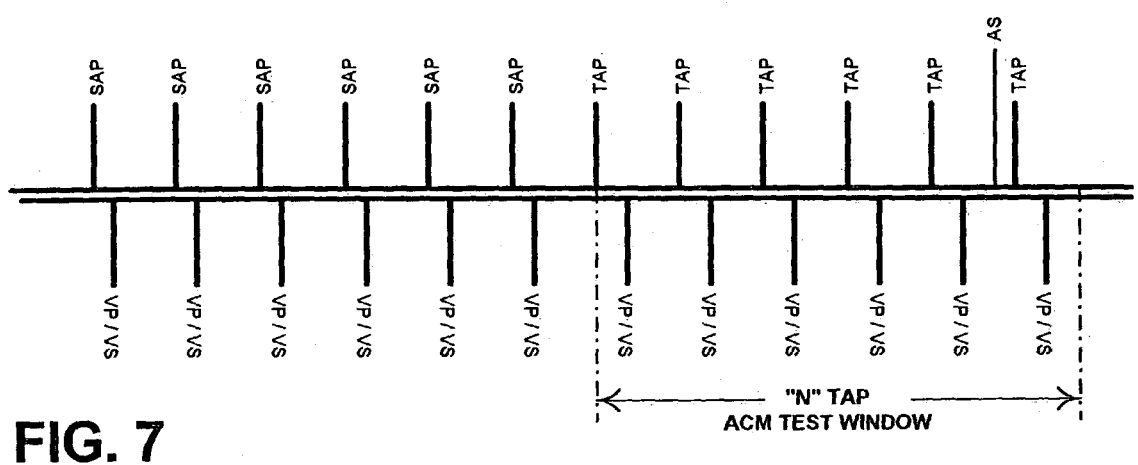
FIG. 7 is a tracing of atrial and ventricular pace and sense events illustrating the ACM algorithm of FIG. 6.
Figure 9:
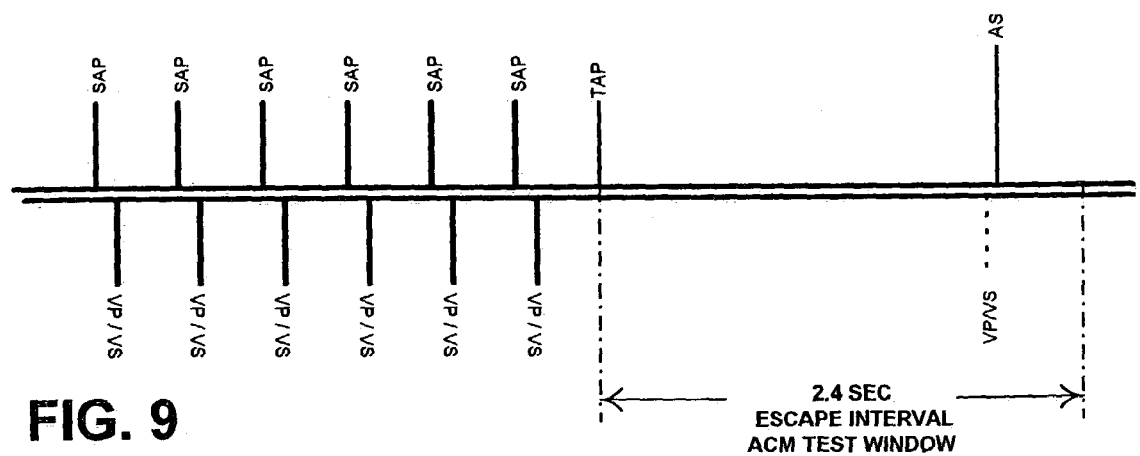
FIG. 9 is a tracing of atrial and ventricular pace and sense events illustrating the ACM algorithm of FIG. 8.
Figure 6:
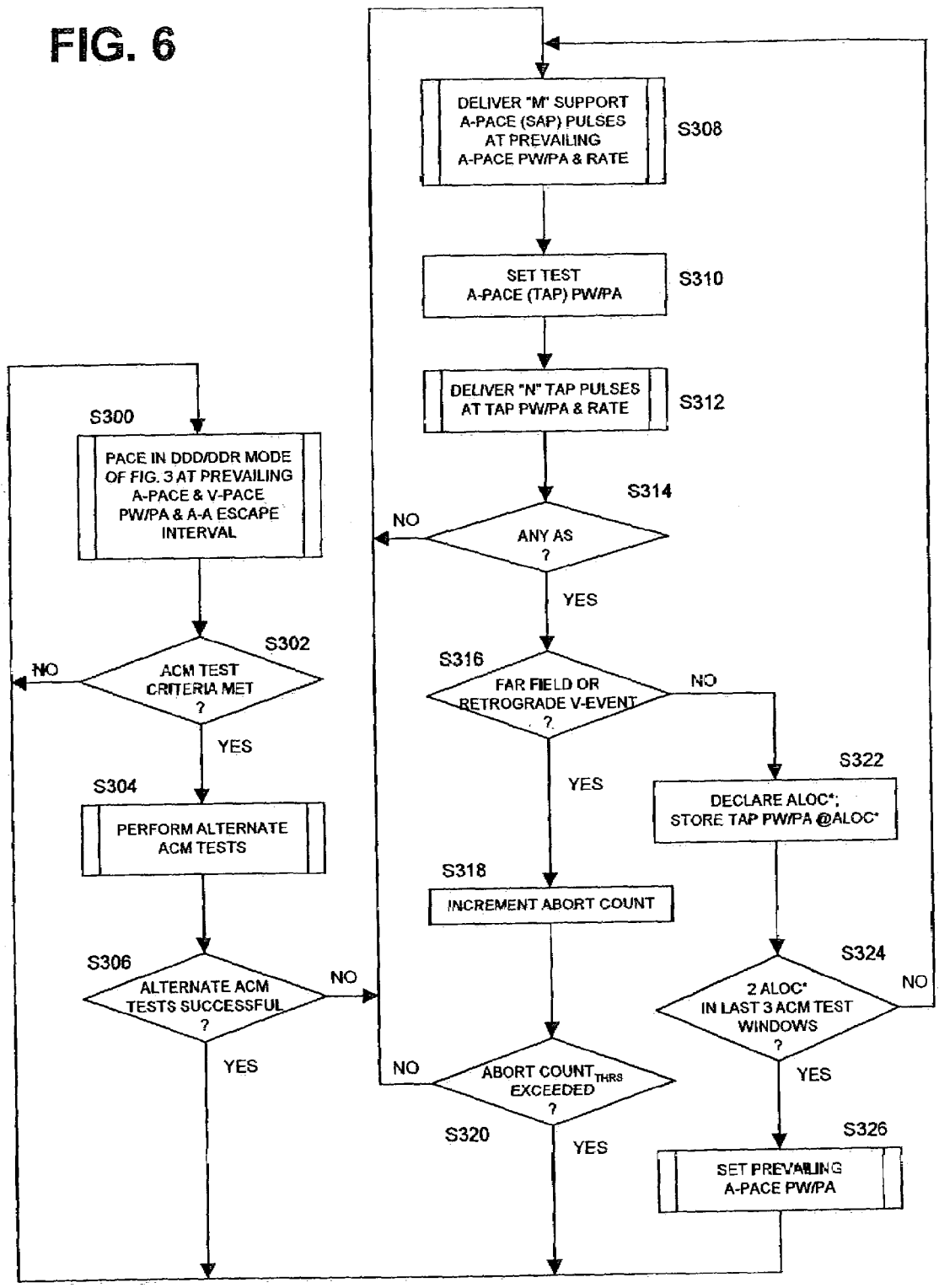
FIG. 6 is a detailed flow chart depicting a further embodiment of an ACM algorithm of the present invention.
Figure 8:
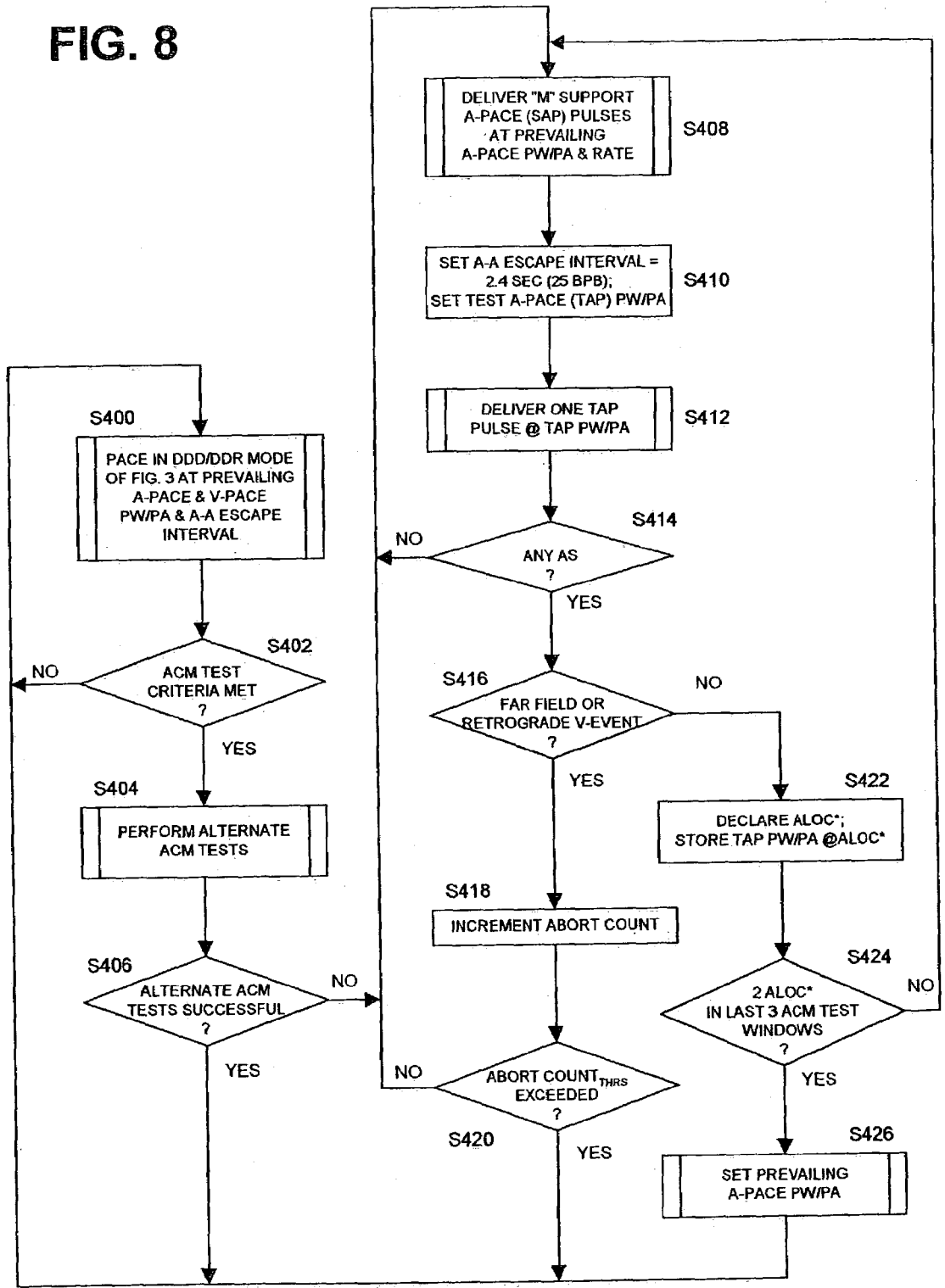
FIG. 8 is a detailed flow chart depicting another embodiment of an ACM algorithm of the present invention.

Steps S208, S308, and S408 of the ACM algorithms of FIGS. 4, 6, and 8, respectively, use a support cycle method comprising delivering a plurality "M" of support A-PACE pulses (designated SAP in the tracings of FIGS. 5, 7, and 9) preceding the delivery of one or more test A-PACE pulses (designated TAP in FIGS. 5, 7, and 9). The M SAP pulses are delivered at the current or programmed A-PACE pulse energy preceding commencement of the ACM algorithm. The TAP pulse width or pulse amplitude is then set in steps S210, S310, and S410 of the ACM algorithms of FIGS. 4, 6, and 8, respectively. At the outset, the TAP pulse width or pulse amplitude is preferably decremented to a starting TAP pulse width, and then decremented during succeeding cycles until ALOC and then or maintained at the decremented AP pulse width or pulse amplitude or decremented further until 2 of 3 successively delivered TAP pulses result in ALOC.

In the first ACM algorithm of FIG. 4, a series of test A-PACE pulses each designated TAP in FIG. 5 are delivered in step S212 over about a 2.4 second ACM test window that corresponds to a slow intrinsic atrial heart rate of 25 bpm.

The ACM test window can be programmed by the physician to reflect the measured slow intrinsic atrial heart rate. Slightly longer or shorter ACM test window durations can be utilized, but 2.4 seconds is a good trade-off between uncovering A-EVENT and interrupting normal pacing too long. The occurrence of a refractory or non-refractory A-EVENT (designated AS in FIG. 5) during the ACM test window signifies that the series of TAP pulses have not resulted in A-CAPTURE, allowing the atria to depolarize at the slow intrinsic atrial heart rate, unless the A-EVENT is deemed to represent far field sensing of a ventricular depolarization or a retrograde conduction of a ventricular depolarization. The prevailing pacing mode, e.g., the DDD pacing mode, can remain unchanged, whereby atrial sensing and synchronized ventricular pacing and sensing (designated VPNS in the tracing of FIG. 5) can continue. The prevailing pacing escape interval can also remain unchanged. For example, three test A-PACE pulses would be delivered if the prevailing pacing rate is 75 bpm. The post-ventricular and post-atrial blanking and refractory periods continue to be timed out as described above with respect to FIG. 3.

In general terms, ALOC is declared if a refractory AR-EVENT or non-refractory A-EVENT (collectively designated "AS" in the figures) occurs during the delivery of the TAP pulses as determined in step S214 that is not due to a retrograde conducted ventricular depolarization due to sensing of the far field R-wave as determined in step S216. Such an AS occurring toward the end of the ACM test window satisfying step S214 is shown in FIG. 5. It is then necessary to make certain that the AS is not closely timed to the delivery of a V-PACE or an R-wave that would typically be detected resulting in a V-EVENT. Thus, it is necessary to determine the interval between the AS and the closest in time V-PACE and V-EVENT and to disregard the AS if the interval is shorter than a threshold interval. Any of the various known techniques for ascertaining that the AS is due to retrograde conduction or far field sensing of ventricular depolarizations can be employed in step S216.

The abort count is incremented in step S218 if the AS is determined to be due to retrograde conduction or far field sensing of ventricular depolarizations in step S216. Steps S208–S216 are repeated employing the same test A-PACE PW and PA if the abort count does not match or exceed a threshold as determined in step S220. The abort count is again incremented in step S218 if the AS is determined to be due to retrograde conduction or far field sensing of ventricular depolarizations in step S216. The ACM is halted and normal pacing is resumed in step S200 if the abort count does match or exceed a threshold as determined in step S220. The abort count can also be incremented for a variety of reasons including those described in the above-referenced U.S. patent application Ser. Nos. 10/004,164 and 10/434,689.

Preferably, a provisional declaration of ALOC (ALOC*) is declared in step S222 if an AS occurs during the delivery of the TAP pulses as determined in step S214 that is not due to a retrograde conducted ventricular depolarization due to sensing of the far field R-wave as determined in step S216. A final ALOC declaration is made when the AS of the slow intrinsic atrial heart rate is detected within the ACM test window in repeated delivery of the test A-PACE pulses and time-out of the ACM test window. Therefore, the TAP PW or PA data is also temporarily stored in step S222 when step S214 is satisfied and step S216 is not satisfied. The new prevailing P-PACE PW and PA are formulated in step S226 when ALOC* is declared in 2 out of 3 (for example) repetitions of steps S208–S222 at the same TAP PW or PA as determined and controlled in step S224.

If both the TAP PW at ALOC and TAP PA at ALOC are to be determined, then the ACM algorithm steps S208–S224 are repeated following the above-described sequence to determine the rheobase and chronaxie ALOC data that are used in step S226 to formulate the prevailing A-PACE PW and PA employed in step S200 until the next time that the ACM algorithm is invoked following steps S202–S206.

In the second ACM algorithm depicted in FIGS. 6 and 7, steps S300–S310 are followed in the same manner as steps S200–S210, as described above. In this algorithm, "N" test A-PACE pulses each designated TAP in FIG. 7 are delivered in step S312 wherein the number N and the TAP escape interval extend over an effective ACM test window that can correspond to a slow intrinsic atrial heart rate of 25 bpm or less. The TAP escape interval can be the same or different than the prevailing A-A escape interval. The number N and the TAP escape interval that define the ACM test window length can also be programmed by the physician to reflect the measured slow intrinsic atrial heart rate. The prevailing pacing mode, e.g., the DDD pacing mode, can remain unchanged, whereby atrial sensing and synchronized ventricular pacing and sensing (designated VPNS in the tracing of FIG. 7) can continue. For example, if the TAP rate is 75 bpm, then N=3–6, for example. Then, steps S314–S326 are followed in the same manner as steps S214–S226, as described above.

The post-ventricular and post-atrial blanking and refractory periods continue to be timed out as described above with respect to FIG. 3 upon delivery of each test A-PACE pulse and each V-PACE pulse, if delivered, during the ACM test window defined in steps S212 and S312 and shown in FIGS. 5 and 7. Therefore, there is some possibility that an intrinsic atrial depolarization could occur during an atrial sense amplifier blanking period resulting in failure to declare an A-EVENT. The ACM algorithm illustrated in FIGS. 8 and 9 minimizes this possibility by delivering only one test A-PACE pulse and then extends the pacing escape interval In the third ACM algorithm depicted in FIGS. 8 and 9, steps S400–S410 are followed in the same manner as steps S200–S210, as described above. Additionally, the A-A pacing escape interval that is to be timed out from the last delivered test A-PACE pulse is set to correspond to a 2.4 second ACM test window in step S410. In this case, the last delivered test A-PACE pulse is the only delivered test A-PACE pulse. In step S412, preferably one TAP pulse is delivered upon time-out of the prevailing A-A escape interval from the last delivered SAP pulse. The prolonged A-A escape interval is then timed out from the delivered TAP pulse, whereby atrial and ventricular pacing is suppressed over the ACM test window. Then, steps S314–S326 are followed in the same manner as steps S214–S226, as described above. Any A-EVENT detected during time out of the ACM test window defined by the prolonged escape interval signifies that the TAP pulse energy did not result in A-CAPTURE, allowing the atria to depolarize at the slow intrinsic atrial heart rate, unless the A-EVENT is deemed to represent far field sensing of a ventricular depolarization or a retrograde conduction of a ventricular depolarization as described above.

An example of a retrograde conduction of or far field sensing of a ventricular R-wave applicable to all the ACM algorithms is also illustrated in FIG. 9. The V-EVENT (designated VS and depicted in broken lines in the tracing of FIG. 9) occurs simultaneously or so close in time to an A-EVENT designated AS, then it is declared to be a concluded to be a retrograde conduction of or far field sensing of a ventricular R-wave.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. In a pacing system adapted to be implanted in a patient's body to provide atrial pacing at an atrial pacing rate exceeding a slow intrinsic atrial heart rate insufficient to provide adequate cardiac output comprising an implantable pulse generator, an atrial lead extending from the implantable pulse generator having at least one active atrial pace/sense electrode adapted to be disposed in operative relation to an atrial heart chamber, and an indifferent atrial pace/sense electrode adapted to be implanted in the patient's body, the implantable pulse generator further comprising:

atrial pace pulse generator means coupled to the active and indifferent atrial pace sense electrodes for delivering an atrial pace (A-PACE) pulse having an A-PACE pulse width and an A-PACE pulse amplitude to the atrial heart chamber;

atrial sensing means coupled to the active and indifferent atrial pace/sense electrodes for sensing intrinsic atrial depolarizations and declaring an A-EVENT;

A-A escape interval timing means for timing out an A-A escape interval following generation of an A-PACE pulse by said atrial pulse generator means and following an A-EVENT declared by the atrial sensing means; and means for triggering said atrial pulse generator means to generate an A-PACE pulse at the expiration of the A-A escape interval whereby the atrial heart chamber is paced in the absence of an A-EVENT declared during the A-A escape interval, an atrial capture management (ACM) method for periodically determining an A-PACE pulse energy sufficient to reliably capture the atrium without being wasteful of battery energy from a test A-PACE pulse energy at atrial loss of capture (ALOC) further comprising:

defining an ACM test window exceeding a prevailing A-A escape interval and correlated to the slow intrinsic atrial heart rate;

setting the A-PACE pulse energy of a test A-PACE pulse;

triggering the atrial pace pulse generator means to deliver at least one test A-PACE pulse at the test A-PACE pulse energy during the ACM test window;

timing out the ACM test window;

declaring ALOC by the delivered test A-PACE pulse at the test A-PACE pulse energy if an A-EVENT is declared during the time-out of an ACM test window;

declaring atrial capture by the delivered test A-PACE pulse at the test A-PACE pulse energy in the absence of an A-EVENT declared during the ACM test window; and setting the prevailing A-PACE pulse energy as a function of the test A-PACE pulse energy at ALOC.

2. The method of claim 1, further comprising the steps of:
   determining if an A-EVENT detected during the ACM test window is likely due to one of retrograde conduction of or far field sensing of a ventricular depolarization; and
   withholding the declaration of ALOC if the A-EVENT is likely due to one of retrograde conduction of or far field sensing of a ventricular depolarization.

3. The method of claim 2, wherein the step of defining an ACM test window comprises changing the A-A escape interval to follow generation of a test A-PACE pulse by said atrial pulse generator means from the prevailing A-A escape interval to a prolonged A-A escape interval correlated to the slow intrinsic atrial heart rate.

4. The method of claim 2, wherein the triggering step further comprises triggering the atrial pace pulse generator means to deliver at least one additional test A-PACE pulse at the test A-PACE pulse energy during the ACM test window.

5. The method of claim 4, wherein the timing step comprises counting a plurality of delivered test A-PACE pulses at the test A-PACE pulse energy and halting the time-out of the ACM test window when a predetermined number of test A-PACE pulses are delivered.

6. The method of claim 2, wherein the ACM steps are repeated in a sequence to determine the test A-PACE pulse width and/or the test A-PACE pulse amplitude at ALOC.

7. The method of claim 1, wherein the step of defining an ACM test window comprises changing the A-A escape interval to follow generation of a test A-PACE pulse by said atrial pulse generator means from the prevailing A-A escape interval to a prolonged A-A escape interval correlated to the slow intrinsic atrial heart rate.

8. The method of claim 1, wherein the triggering step further comprises triggering the atrial pace pulse generator means to deliver at least one additional test A-PACE pulse at the test A-PACE pulse energy during the ACM test window.

9. The method of claim 8, wherein the timing step comprises counting a plurality of delivered test A-PACE pulses at the test A-PACE pulse energy and halting the time-out of the ACM test window when a predetermined number of test A-PACE pulses are delivered.

10. The method of claim 1, wherein the ACM steps are repeated in a sequence to determine the test A-PACE pulse width and/or the test A-PACE pulse amplitude at ALOC.

11. The method of claim 1, wherein the ACM method further comprises the step of delivering a plurality of support A-PACE pulses at the prevailing A-A escape interval.

12. In a pacing system adapted to be implanted in a patient's body to provide atrial pacing at an atrial pacing rate exceeding a slow intrinsic atrial heart rate insufficient to provide adequate cardiac output comprising an implantable pulse generator, an atrial lead extending from the implantable pulse generator having at least one active atrial pace/sense electrode adapted to be disposed in operative relation to an atrial heart chamber, and an indifferent atrial pace/sense electrode adapted to be implanted in the patient's body, the implantable pulse generator further comprising:
   atrial pace pulse generator means coupled to the active and indifferent atrial pace sense electrodes for delivering an atrial pace (A-PACE) pulse having an A-PACE pulse width and an A-PACE pulse amplitude to the atrial heart chamber;

atrial sensing means coupled to the active and indifferent atrial pace/sense electrodes for sensing intrinsic atrial depolarizations and declaring an A-EVENT;

A-A escape interval timing means for timing out an A-A escape interval following generation of an A-PACE pulse by said atrial pulse generator means and following an A-EVENT declared by the atrial sensing means; and means for triggering said atrial pulse generator means to generate an A-PACE pulse at the expiration of the A-A escape interval whereby the atrial heart chamber is paced in the absence of an A-EVENT declared during the A-A escape interval, atrial capture management (ACM) means for periodically determining an A-PACE pulse energy sufficient to reliably capture the atrium without being wasteful of battery energy from a test A-PACE pulse energy at atrial loss of capture (ALOC) further comprising:

ACM test window defining means for defining an ACM test window exceeding the A-A escape interval and correlated to the slow intrinsic atrial heart rate;

means for setting the A-PACE pulse energy of a test A-PACE pulse;

means for triggering the atrial pace pulse generator means to deliver at least one test A-PACE pulse at the test A-PACE pulse energy;

means for timing out the ACM test window;

means responsive to an A-EVENT declared during the time-out of the ACM test window for declaring ALOC by the delivered test A-PACE pulse at the test A-PACE pulse energy;

means responsive to the absence of an A-EVENT declared during the ACM test window for declaring atrial capture by the delivered test A-PACE pulse at the test A-PACE pulse energy; and means for setting the prevailing A-PACE pulse energy as a function of the test A-PACE pulse energy at ALOC.

13. The pacing system of claim 12, further comprising:

means for determining if an A-EVENT detected during the ACM test window is likely due to one of retrograde conduction of or far field sensing of a ventricular depolarization; and means for withholding the declaration of ALOC if the A-EVENT is determined to be likely due to one of retrograde conduction of or far field sensing of a ventricular depolarization.

14. The pacing system of claim 13, wherein the means for defining an ACM test window comprises means for changing the A-A escape interval to follow generation of a test A-PACE pulse by said atrial pulse generator means from a prevailing A-A escape interval to a prolonged A-A escape interval correlated to the slow intrinsic atrial heart rate.

15. The pacing system of claim 13, wherein the triggering means further comprises means for triggering the atrial pace pulse generator means to deliver at least one additional test A-PACE pulse at the test A-PACE pulse energy during the ACM test window.

16. The pacing system of claim 15, wherein the timing means comprises means for counting a plurality of delivered test A-PACE pulses at the test A-PACE pulse energy and halting the time-out of the ACM test window when a predetermined number of test A-PACE pulses are delivered.

17. The pacing system of claim 13, wherein the ACM means repeats operation in a sequence to determine the test A-PACE pulse width and/or the test A-PACE pulse amplitude at ALOC.

18. The pacing system of claim 12, wherein the means for defining an ACM test window comprises means for changing the A-A escape interval to follow generation of a test A-PACE pulse by said atrial pulse generator means from a prevailing A-A escape interval to a prolonged A-A escape interval correlated to the slow intrinsic atrial heart rate.

19. The pacing system of claim 12, wherein the triggering means further comprises means for triggering the atrial pace pulse generator means to deliver at least one additional test A-PACE pulse at the test A-PACE pulse energy during the ACM test window.

20. The pacing system of claim 19, wherein the timing means comprises means for counting a plurality of delivered test A-PACE pulses at the test A-PACE pulse energy and halting the time-out of the ACM test window when a predetermined number of test A-PACE pulses are delivered.

21. The pacing system of claim 12, wherein the ACM means repeats operation in a sequence to determine the test A-PACE pulse width and/or the test A-PACE pulse amplitude at ALOC.

22. The pacing system of claim 12, wherein the ACM means further comprises means for delivering a plurality of support A-PACE pulses at the prevailing A-A escape interval.

* * * * *